(12) United States Patent
Seifert et al.

(10) Patent No.: US 6,395,908 B1
(45) Date of Patent: May 28, 2002

(54) PROCESS FOR THE PREPARATION OF VINYLENE CARBONATE, AND THE USE THEREOF

(75) Inventors: Bernhard Seifert, Ober-Ramstadt; Sylvia Becker, Seeheim-Jugenheim; Mark Neuschütz, Darmstadt, all of (DE)

(73) Assignee: Merck Patentgesellschaft, Darmstadt (DE)

( * ) Notice: Subject to any disclaimer, the term of this patent is extended or adjusted under 35 U.S.C. 154(b) by 0 days.

(21) Appl. No.: 09/715,048

(22) Filed: Nov. 20, 2000

(30) Foreign Application Priority Data

Nov. 19, 1999 (DE) .......................................... 199 55 944

(51) Int. Cl.$^7$ ............................................ C07D 317/10
(52) U.S. Cl. ..................................................... 549/229
(58) Field of Search ......................................... 549/229

(56) References Cited

U.S. PATENT DOCUMENTS 4,353,831 A * 10/1982 Strege et al. ................ 549/229
5,391,767 A * 2/1995 Mais et al. .................. 549/229

OTHER PUBLICATIONS

Newman et al (1955): J. Am. Chem. Soc. vol. 77, 3789–3793.*

* cited by examiner

*Primary Examiner*—T. A. Solola
*Assistant Examiner*—Golam M. M. Shameem
(74) *Attorney, Agent, or Firm*—Millen, White, Zelano & Branigan, P.C.

(57) ABSTRACT

The invention relates to a process for the preparation of vinylene carbonate of the formula (I)

(I)

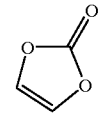

by reacting a monohaloethylene carbonate of the formula (II)

(II)

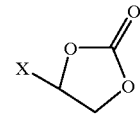

in which X is a halogen atom, with a dehydrohalogenating agent at elevated temperature in the presence of an organic solvent, characterized in that the organic solvent employed is ethylene carbonate.

The process according to the invention enables vinylene carbonate to be prepared in a simple manner and in high yield. The vinylene carbonate prepared in accordance with the invention can be used for various applications.

15 Claims, No Drawings

PROCESS FOR THE PREPARATION OF VINYLENE CARBONATE, AND THE USE THEREOF

SUMMARY OF THE INVENTION

The present invention relates to a process for the preparation of vinylene carbonate, and to the use of the vinylene carbonate prepared, for example as an additive for lithium ion batteries, as a component of surface coatings or as a monomer for the preparation of polyvinylene carbonate.

J. Am. Chem. Soc., 77, 3789–3793 (1955) discloses a process for the preparation of vinylene carbonate in which, in a first synthesis step, monochloroethylene carbonate is prepared by chlorination of ethylene carbonate. In a second step, a solution of monochloroethylene carbonate in ether is reacted with triethylamine overnight under ref lux to give vinylene carbonate by elimination of hydrogen chloride. After removal of the ether and distillation, crude vinylene carbonate is obtained in a yield of 59%, and is purified by further rectification. Disadvantageous features of this process are thus the long reaction times, the relatively complex work-up of the reaction product for removal of undesired components, such as solvents, and the relatively low yield of the target product.

The present invention provides a process which enables, in a simple and economical manner, the preparation of vinylene carbonate in high yields.

The invention thus relates to a process for the preparation of vinylene carbonate of the formula (I)

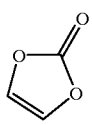

(I)

by reacting a monohaloethylene carbonate of the formula (II)

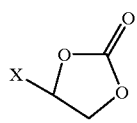

(II)

in which X is a halogen atom(e.g., Br, Cl, F, I), with a dehydrohalogenating agent, preferably at elevated temperature in the presence of an organic solvent, which is characterized in that the organic solvent employed is ethylene carbonate.

The ether used in the conventional process is replaced in the process according to the invention by ethylene carbonate as solvent in the dehydrohalogenation reaction. This reduces the number of interfering compounds present in the reaction mixture and thus simplifies work-up of the reaction mixture. Furthermore, significantly higher yields are achieved in the process according to the invention compared with the known process. For certain applications, for example as solvent for non-aqueous electrolytes in lithium ion batteries, it is not necessary to separate off the ethylene carbonate present in the reaction mixture, but instead a vinylene carbonate/ethylene carbonate mixture of this type is virtually desired for this use. Experiments have shown that vinylene carbonate is highly temperature-sensitive and can decompose within hours at temperatures above 60° C. and even within minutes at above 80° C. However, elimination reactions generally proceed in higher yields at higher temperatures. It has been shown in accordance with the invention that the dehydrohalogenation reaction here can favorably be carried out at temperatures in the range 40–80° C., preferably at about 60° C., although lower (e.g., room temperature) or higher temperatures are possible. In this case, the reaction can be completed within a period of 1–4 hours, preferably within about 2 hours. Under such reaction conditions, the yield of crude vinylene carbonate is usually greater than 80%. Preferably, a ratio of monohaloethylene carbonate: dehydrohalogenating agent from 1:1 to 1:2, more preferably 1:1.5, is used. The monohaloethylene carbonate is preferably 99.5% pure, with <0.01% glycol, e.g., ethylene glycol.

Conventional dehydrohalogenating agents, for example alkali metal hydroxide solutions, amines, alkylamides or heterocyclic nitrogen compounds, can be employed for the process according to the invention. Preference is given to trialkylamines, particularly preferably triethylamine. Preferably the dehydrohalogenation agent is 99% pure.

The process according to invention proceeds particularly favorably in the presence of monochloroethylene carbonate as monohaloethylene carbonate of the above formula (II).

It is furthermore particularly advantageous to use an inert gas atmosphere for the reaction according to the invention in order to avoid decomposition reactions. Examples of suitable protective gases are nitrogen and noble gases, such as argon. The use of a stabilizer which is usually employed for the vinylene carbonate obtained as reaction product is thus unnecessary.

For a complete and uniform reaction, it is furthermore advantageous to ensure good mixing of the reaction components.

The monohaloethylene carbonates employed as starting compounds according to the invention are known compounds which can be prepared, for example, by photochemical halogenation or by azoisobutyronitrile-(AIBN-)initiated halogenation of ethylene carbonate using, for example, sulfuryl chloride. Residual amounts of AIBN or sulfuryl chloride in the monohaloethylene carbonate are permissible here. Residual amounts of sulfuryl chloride present can be eliminated in the process according to the invention, for example by using a corresponding excess of dehydrohalogenating agent, such as triethylamine.

Whereas in the conventional process the work-up of the crude vinylene carbonate obtained is carried out by simple distillation, it has been found in accordance with the invention that undesired reductions in yield can occur in this case. Preferably, therefore, a work-up process which ensures that the vinylene carbonate remains at the corresponding evaporation temperature for the shortest possible time is employed in accordance with the invention. This is achieved, for example, by means of vacuum distillation in a thin-film evaporator at bath temperatures of about 100° C. and a pressure of about 5 mbar. This enables vinylene carbonate to be obtained directly from the dehydrohalogenation reaction product as a colorless product in a yield of about at least 75%.

The vinylene carbonate prepared in the process according to the invention can be employed for various applications, for example as an additive for lithium ion batteries, e.g. as solvent for non-aqueous electrolytes, (U.S. Pat. Nos. 5,626,981, 5,712,059 and 5,352,548) as a component of surface coatings or as a monomer for the preparation of polyvinylene carbonate. In the latter polymerization, high-molecular-weight, colorless polymers can be obtained which give water-soluble polymers through a subsequent hydrolysis reaction.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and of corresponding German application No. DE 199 55 944.9, filed Nov. 19, 1999 is hereby incorporated by reference.

EXAMPLES

Example 1

A 250 ml twin-jacket, four-neck apparatus equipped with precision glass stirrer, stirrer motor, coil condenser, dropping funnel and thermometer in the liquid phase is flushed with argon. 0.420 mol of chloroethylene carbonate and 84 ml of ethylene carbonate (anhydrous) are then introduced with continued flushing with argon. The internal temperature is raised to 57.6° C. by means of a heating bath. 0.630 mol of triethylamine are then added dropwise via a dropping funnel over the course of 25 minutes with stirring, during which the internal temperature is kept at between 56 and 59° C. When the addition of the triethylamine is complete, the reaction mixture is stirred at about 60° C. for 1 hour. Excess triethylamine is then distilled off on a rotary evaporator at a bath temperature of 40° C. and a pressure of 150 mbar. The amount of vinylene carbonate present in the crude vinylene carbonate mixture is 77.2% of theory.

Comparative Example 1

Vinylene carbonate is prepared by the process described in J. Am. Chem. Soc. 77, 3789–3793 (1955). To this end, the apparatus described in Example 1 is flushed with argon. 0.280 mol of chloroethylene carbonate and 33.4 ml of tert-butyl methyl ether (ultra-pure) are then introduced into the apparatus while flushing with argon, and the mixture is warmed to 37.8° C. by means of a heating bath. 0.350 mol of triethylamine are then added dropwise via a dropping funnel over the course of 50 minutes with stirring, during which the internal temperature is kept at between 37 and 40° C. The reaction mixture is then kept at about 40° C. for 50 minutes with stirring. The amount of vinylene carbonate present in the crude vinylene carbonate mixture is only 26.6% of theory.

Example 2

The crude vinylene carbonate mixture obtained in Example 1 is worked up by vacuum distillation in a thin-film evaporator (internal diameter: 40 mm, rotor length: 25 cm). The bath temperature is about 100° C. and the pressure is about 5 mbar. At a feed rate of about 3 ml/min, a clear, slightly yellowish, oil-like distillate is obtained after about 70 minutes. The yield of purified vinylene carbonate here is 73.3%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to-various usages and conditions.

What is claimed is:

1. A process for the preparation of vinylene carbonate of formula (I)

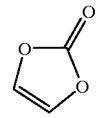

(I)

comprising reacting a monohaloethylene carbonate of formula (II)

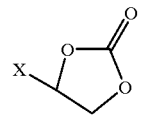

(II)

in which X is a halogen atom, with a dehydrohalogenating agent at elevated temperature in the presence of an organic solvent comprising ethylene carbonate.

2. The process according to claim 1, carried out at a temperature of 40–80° C.

3. The process according to claim 1, carried out at a temperature of 60° C.

4. The process according to claim 1, carried out for 1 to 4 hours.

5. The process according to claim 1, carried out for 2 hours.

6. The process according to claim 1, wherein the dehydrohalogenating agent comprises an alkali metal solution, an amine, an alkylamide or a heterocyclic nitrogen compound.

7. The process according to claim 1, wherein the dehydrohalogenating agent comprises a trialkylamine.

8. The process according to claim 1, wherein the dehydrohalogenating agent comprises triethylamine.

9. The process according to claim 1, wherein the monohaloethylene carbonate comprises monoethylene carbonate.

10. The process according to claim 1, wherein the reaction is carried out under an inert gas atmosphere.

11. The process according to claim 1, further comprising separating vinylene carbonate by distillation.

12. The process according to claim 1, further comprising separating vinylene carbonate by vacuum distillation in a thin-film evaporator.

13. The process according toe claim 12, wherein the process is carried out at a bath temperature of about 100° C. and a pressure of about 5 mbar.

14. The process according to claim 1, wherein the vinylene carbonate and the ethylene carbonate is not separated from vinylene carbonate.

15. The process according to claim 1, further comprising introducing into a cell an electrolyte containing said vinylene carbonate and said ethylene carbonate, to form a lithium ion battery.

* * * * *